(12) United States Patent
Dakka et al.

(10) Patent No.: US 7,718,564 B2
(45) Date of Patent: May 18, 2010

(54) PARTIALLY DECOMPOSED CATALYST AND HYDROCARBON OXIDATION PROCESSES USING THE SAME

(75) Inventors: Jihad Mohammed Dakka, Whitehouse Station, NJ (US); Sabato Miseo, Pittstown, NJ (US); Stuart Leon Soled, Pittstown, NJ (US); Jose Guadalupe Santiesteban, Baton Rouge, LA (US); Joseph Ernest Baumgartner, Califon, NJ (US); Michiel Christian Alexander Van Vliet, Delft (NL); Roger Arthur Sheldon, Rijswijk (NL)

(73) Assignee: ExxonMobil Research and Engineering Company, Annandale, NJ (US)

( * ) Notice: Subject to any disclaimer, the term of this patent is extended or adjusted under 35 U.S.C. 154(b) by 528 days.

(21) Appl. No.: 11/434,717

(22) Filed: May 16, 2006

(65) Prior Publication Data
US 2006/0293544 A1    Dec. 28, 2006

Related U.S. Application Data

(60) Provisional application No. 60/693,732, filed on Jun. 24, 2005.

(51) Int. Cl.
*B01J 23/72* (2006.01)
*B01J 23/755* (2006.01)
*B01J 31/00* (2006.01)
*B01J 27/24* (2006.01)

(52) U.S. Cl. .................. 502/113; 502/150; 502/165; 502/167; 502/400; 502/405

(58) Field of Classification Search .............. 502/113, 502/150, 165, 167, 400, 405
See application file for complete search history.

(56) References Cited

U.S. PATENT DOCUMENTS

| 5,210,269 A | 5/1993 | DiMuzio et al. |
|---|---|---|
| 5,498,743 A | 3/1996 | Shih et al. |
| 5,536,864 A | 7/1996 | Paret et al. |
| 5,550,278 A | 8/1996 | Rechner et al. |
| 5,686,644 A | 11/1997 | Rivetti et al. |
| 5,958,821 A | 9/1999 | Ishii et al. |
| 6,002,026 A | 12/1999 | Groves et al. |
| 6,008,399 A | 12/1999 | Chang et al. |
| 6,555,715 B1 | 4/2003 | Kocal et al. |
| 2003/0083527 A1 | 5/2003 | Kuhnle et al. |
| 2004/0024248 A1 | 2/2004 | Ishii et al. |

FOREIGN PATENT DOCUMENTS

| JP | 2000119225 A | 4/2000 |
|---|---|---|
| JP | 2002282698 | 2/2002 |
| WO | WO 2004/045767 A2 | 6/2004 |
| WO | WO 2004/046076 A2 | 6/2004 |

OTHER PUBLICATIONS

Hughes et al. Nature, 2005, 437(20), 1132-1135.*
White, M. Chapter 3 in Catalysis, vol. 18; Spivey, J. J. (Editor), published Feb. 28, 2005.*
Kenvin et al. Journal of Catalysis Aug. 1991, 130(2), 447-458 (the abstract is provided).*

* cited by examiner

*Primary Examiner*—Rebecca L Anderson
*Assistant Examiner*—Jason M Nolan
(74) *Attorney, Agent, or Firm*—Robert A. Migliorini

(57) ABSTRACT

The present invention is related to a hydrocarbon oxidation process. The process comprises bringing one or more hydrocarbons into contact with a source of oxygen in the presence of a radical initiator and a catalyst. The catalyst comprises an organic metal complex located on a catalyst support, and is obtained by partial decomposition of the organic metal complex. For example, the process can be used to produce dimethyl carbonate from dimethoxy methane. The invention is also related to a partially decomposed catalyst that comprises a silica support and an organic metal complex, wherein at least 5% of the organic compound remains in the catalyst. The organic metal complex comprises an organic compound and a metal-based compound wherein the metal is selected from copper, nickel, and combinations thereof. The invention is also related to a process for manufacturing of a catalyst comprising mixing L-arginine, a Cu-based compound, water, and optionally another metal-based compound to form a solution; impregnating the solution onto a silica support to form a catalyst precursor; and partially decomposing the L-arginine to form the catalyst so that at least 5% of L-arginine remains in the catalyst.

45 Claims, 2 Drawing Sheets

PARTIALLY DECOMPOSED CATALYST AND HYDROCARBON OXIDATION PROCESSES USING THE SAME

CROSS REFERENCE TO RELATED APPLICATION

This application claims the benefit of U.S. Provisional Application No. 60/693,732 filed Jun. 24, 2005.

FIELD OF THE INVENTION

The present invention is directed generally to a process for the oxidation of hydrocarbons using a partially decomposed catalyst. The present invention also relates to the partially decomposed catalyst used in such process, and to a process for making such catalyst.

BACKGROUND

Hydrocarbon oxidation is an established process in the chemical and petroleum refining industries, and many oxidized hydrocarbons are known to have commercial value. For example, organic carbonates, such as dimethyl carbonate (DMC), are known to be valuable as intermediates in many chemical processes and as synthetic lubricants, solvents, plasticizers, and monomers for organic glass and various polymers, such as polycarbonate.

A common method for producing dimethyl carbonate is the oxidative carbonylation of methanol. A disadvantage associated with this method is the corrosive nature of copper and bromine catalysts used. Another disadvantage is the incomplete conversion of the starting alcohol, which can lead to the formation of methanol/DMC azeotropes and subsequent difficulties in downstream processing.

Several alternative processes have been proposed, such as the formation of DMC from methanol and supercritical $CO_2$. However, the reaction conditions are harsh and a large amount of molecular sieve is required to obtain a significant conversion.

Of particular importance in all oxidation processes is the degree of conversion of the starting materials and the selectivity of conversion into the desired products. Thus, there is a need for efficient processes for the oxidation of hydrocarbons, and in particular for the oxidation of dimethoxy methane (DMM) to dimethyl carbonate (DMC), which processes are highly selective and/or have high degrees of conversion.

Background references include U.S. Pat. No. 5,536,864 to Paret, et al.; U.S. Pat. No. 5,550,278 to Rechner, et al.; U.S. Pat. No. 5,498,743 to Shih, et al.; U.S. Pat. No. 6,008,399 to Chang, et al.; Japanese Patent No. 20000119225 to Mitsubishi Gas Chem Co; U.S. Pat. No. 6,555,715 to Kocal, et al.; U.S. Patent Application Publication 2003/0083527; Japanese Patent Application Publication No. 2002-282698; U.S. Pat. No. 5,958,821 to Ishii, et al.; and PCT Publications WO2004/046076 and WO2004/045767; the entire disclosures of which are hereby incorporated herein by reference.

SUMMARY OF THE INVENTION

In one embodiment, the present invention provides a hydrocarbon oxidation process comprising bringing one or more hydrocarbons into contact with a source of oxygen in the presence of a radical initiator and a catalyst. The catalyst comprises an organic metal complex located on a catalyst support, and is obtained by partial decomposition of the organic metal complex.

In another embodiment, the present invention provides a process for producing dimethyl carbonate. The process comprises contacting dimethoxy methane with a source of oxygen in the presence of a radical initiator and a catalyst. The catalyst comprises an organic metal complex located on a catalyst support, and is obtained by partial decomposition of the organic metal complex.

In another embodiment, the present invention provides a partially decomposed catalyst comprising a silica support and an organic metal complex, wherein at least 5% of the organic compound remains in the catalyst. The organic metal complex comprises an organic compound and a metal-based compound wherein the metal is selected from copper, nickel, and combinations thereof.

In yet another embodiment, the present invention provides a process for the manufacture of a catalyst. The process comprises mixing L-arginine, a Cu-based compound, water, and optionally another metal-based compound to form a solution; impregnating the solution onto a silica support to form a catalyst precursor; and partially decomposing the L-arginine to form the catalyst so that at least 5% of L-arginine remains in the catalyst.

DETAILED DESCRIPTION

Catalyst and Method of Preparing

Figure 1:
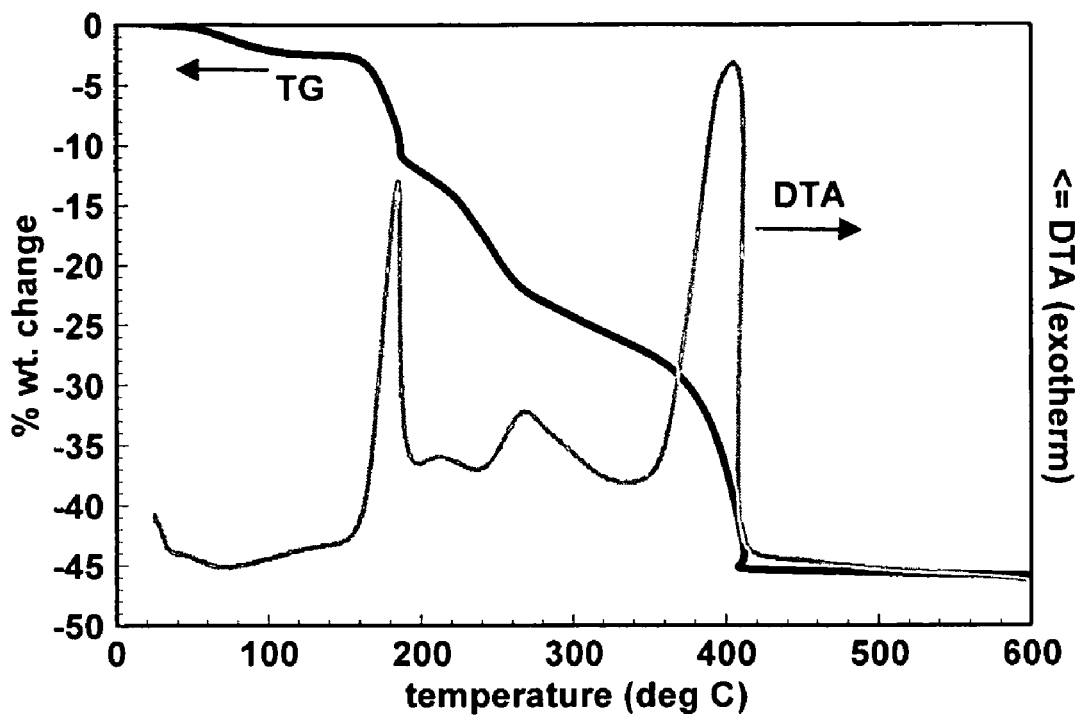
FIG. 1 shows the decomposition pattern of the Cu-arginine complex prepared according to Example 1a, as measured by thermogravimetry/differential thermal analysis (TG/DTA).

In the process of the present invention, hydrocarbons are oxidized in the presence of a radical initiator and a catalyst comprising a partially decomposed organic metal complex. The catalyst is prepared by depositing or forming an organic metal complex in or on a support, and then partially decomposing the complex to produce the final catalyst product. As used herein, the term "remnant" refers to this final catalyst product, i.e., the catalyst support containing the partially decomposed organic metal complex.

The organic metal complex that is used to form the catalyst comprises at least one organic compound and at least one catalytically active metal-based compound. Suitable organic compounds include any organic compound that is capable of forming an organic complex with the one or more catalytically active metals. Preferably, the organic compound is selected to provide metal organic complexes that are stable under the conditions normally used for drying catalyst supports after impregnation with one or more catalytically active metals. Such organic compounds are well known in the art of transition metal chemistry and include, for example, organic chelating agents, organic monodentate, bidentate, and polydentate ligands commonly used in the preparation of transition metal coordination complexes.

In one embodiment, the organic compound contains one or more amino groups such as amines or amino acids. Suitable amines include, for example, aliphatic amines, cycloaliphatic amines, aralkyl amines, and alkaryl amines. Suitable amino acids include natural and synthetic amino acids. The natural amino acids include alanine; arginine; asparagine; aspartic acid; cysteine; cystine; 3,5-dibromotyrosine; 3,5-diiodotyrosine; glutamic acid; glutamine; glycine; histidine; hydroxylysine; hydroxyproline; isoleucine; leucine; lysine; methionine; phenylalanine; proline; serine; threonine; thyroxine; tryptophan; tyrosine; valine; and isomers thereof In a particular embodiment, the amino acid is L-arginine.

In another embodiment, the organic compound contains one or more amino groups and one or more alcohol groups. In a particular aspect of this embodiment, the organic compound is an amino alcohol selected from mono-, di-, and tri-, substituted aliphatic hydroxyalkylamines, N-alkyl-methanolamines, N-alkyl-dimethanolamines, N,N-dialkyl-ethanolamines, N-alkyl-propanolamines, N-alkyl-dipropanolamines, N,N-dialkyl-propanolamines, N-alkyl-butanolamines, N-alkyl-dibutanolamines, N,N-dialkyl-butanolamines, N-alkyl-hexanolamines, N-alkyl-dihexanolamines, N,N-dialkyl-hexanolamines, N-alkyl-heptanolamines, N-alkyl-diheptanolamines, and N,N-dialkyl-heptanolamines. In another particular aspect of this embodiment, the organic compound is a mono-, di-, and tri-substituted aliphatic hydroxyalkylamine selected from methanolamine, di-methanolamine, tri-methanolamine, ethanolamine, di-ethanolamine, tri-ethanolamine, propanolamine, di-propanolamine, tri-propanolamine, butanolamine, di-butanolamine, and tri-butanolamine.

In a particular embodiment, the organic compound is selected from the organic compounds disclosed in PCT publication WO2004/046076, the entire disclosure of which is hereby incorporated herein by reference.

The organic compound may be used at any suitable level in relation to the amount of active metal used, and depends on factors such as the capacity of the metal to complex with the organic compound, the capacity of the organic compound to complex with the metal, and the presence of other complexing ligands such as monodentate ligands. Generally, the organic compound is used at an appropriate mole ratio to convert all of the active metal to one or more organic complexes. However, it is possible to use levels of organic compound which are insufficient to complex with all of the active metal, in which case not all of the metal is converted to organic complex and the resulting catalyst may contain catalytically active metal sites that have been derived from complexed and non-complexed metal intermediates. Generally, the molar ratio of organic compound to active metal is within the range of 0.1:1 to 40:1, or 0.1:1 to 30:1, or 0.2:1 to 25:1, or 0.25:1 to 10:1, or 0.5:1 to 10:1, or 0.25:1 to 5:1, 0.5:1 to 5:1.

Active metal-based compounds that may be used for preparing the organic complex generally comprise one or more Group 3 to Group 12 transition metals, and/or one or more salts thereof. In a particular embodiment, the metal-based compound comprises a metal salt selected from nitrates, nitrosyl nitrates, halides, carbonates, carboxylates, acetylacetonates, chloro complexes, nitro complexes, and amine complexes. In a particular aspect of this embodiment, the metal-based compound comprises a metal salt selected from copper salt, nickel salt, and combinations thereof. In another particular aspect of this embodiment, the metal-based compound comprises a metal salt selected from copper nitrate, nickel nitrate, and combinations thereof.

In a particular embodiment, the active metal-based compound is selected from the metal compounds disclosed in PCT publication WO2004/046076, the entire disclosure of which is hereby incorporated herein by reference.

The support material used to prepare the catalyst of the present invention is selected from a wide variety of porous and non-porous support materials that are well known in the art. The support materials include, but are not limited to alumina, silica, activated carbon, silicon carbide, aluminum oxide, silicon dioxide, titanium dioxide, zirconium dioxide, magnesium oxide, zinc oxide, and combinations thereof. In a particular embodiment, the support material is selected from alumina, silica, and mixtures thereof. In another particular embodiment, the support material is amorphous silica. In another particular embodiment, the support material is ordered mesoporous silica. In a particular aspect of this embodiment, the support material is ordered mesoporous silica designated as M41S, such as MCM-41. In another embodiment, the support material is a crystalline molecular sieve material.

In one embodiment, the catalyst support material contains mesopores, and may be completely mesoporous. In another embodiment, the catalyst support is a mixture of two or more materials, and at least one of the materials is completely or substantially mesoporous. "Mesopore," as used herein, means pores whose diameter is from 2 nm to 50 nm. In another embodiment, the catalyst support material contains macropores. "Macropore," as used herein, means pores whose diameter is greater than 50 nm. In another embodiment, the catalyst support material contains macropores and mesopores.

In a particular embodiment, the catalyst support material is selected from the support materials disclosed in PCT publication WO2004/046076, the entire disclosure of which is hereby incorporated herein by reference.

In the process of forming the catalyst of the present invention, the organic metal complex is deposited or formed on the support material. In one embodiment, the active metal-based compound material is combined with the organic compound material to form a mixture, which is then contacted with a support material to deposit the organic metal complex on the support. In this embodiment, the organic metal complex may be formed on formation of the mixture or may be formed after contact with the support and after removal of any solvent(s) used during formation of the mixture. In another embodiment, the support is first contacted with the active metal-based compound material followed by treatment with the organic compound material to form the organic metal complex on the support. In another embodiment, the support is first contacted with the organic compound material followed by treatment with the active metal-based compound material to form the organic metal complex on the support. In another embodiment, the organic compound material and the active metal-based compound material are contacted simultaneously with the support to form the organic metal complex on the support. In yet another embodiment, a suitable organic metal complex may be synthesized and applied to the support via solution of the complex in a suitable solvent.

The active metal may be exchanged onto the support material, impregnated into it, or physically admixed with it. The application of the individual components or mixture of components may be achieved by steeping the support in an aqueous metal salt solution, or a solution in a suitable solvent of a compound of the metal, or in the mixture. The deposition may be achieved by dipping, spraying, or any other method. Suitable metal salts for preparing the metal salt solutions are, for example, nitrates, nitrosyl nitrates, halides, carbonates, carboxylates, acetylacetonates, chloro complexes, nitrito complexes, and amine complexes of the corresponding metals.

In the case of catalysts which have a plurality of active metals applied to the support, the metal salts or metal salt solutions or metal compound solutions or mixtures may be applied simultaneously or in succession.

When the organic metal complex is formed in a mixture before contact with the support, the mixture is generally formed in combination with a solvent, which may be water, an organic solvent, or a mixture thereof. The amount of solvent used may vary within wide ranges, but is typically sufficient to ensure that the mixture may be effectively contacted with the support so as to wet the support, and to allow penetration of the mixture into the support when the support is porous. Typically, the mixture comprises one or more solvents, which may be present in an amount within the range having a lower limit of 1 wt %, or 5 wt %, or 10 wt %, and an upper limit of 65 wt %, or 70 wt %, or 80 wt %, or 90 wt %, or 99 wt %, based on the total weight of the mixture.

The process for making the catalyst of the present invention is not limited by any particular reactor used. In a particular embodiment, the catalyst is made in a fixed bed, batch, catalytic distillation reactor.

After deposition and/or formation of one or more organic metal complexes in or on the support materials, the complexes are partially decomposed to form the final catalyst product, or "remnant." For purposes of the present invention, the term "partial decomposition" means that the chemical composition of the organic complex is varied, which may be due to a change in the structure of the organic complex or the chemical destruction of part of or a component of the complex.

The method of decomposition is selected to ensure that the removal of non-metal chemical species associated with the complex is incomplete, i.e., at least 5% of the organic compound remains in the catalyst. The partial decomposition is due to variations in structure and/or composition that do not normally occur under the drying conditions typically used in catalyst preparation methods. The changes of structure and/or composition under the conditions of the decomposition procedure may be detected and monitored using various analytical techniques that are well known in the art, such as infra-red spectroscopy, mass spectroscopy, thermogravimetric analysis, gas or liquid chromatography, and spectroscopy.

A variety of methods can be used to induce decomposition of the organic metal complex. In one embodiment, decomposition is induced by a chemical method, such as chemically induced hydrolysis, or by treatment with acid, base, ozone, or similar chemically active materials. In another embodiment, decomposition is induced by a thermal method, such as pyrolysis, calcination, or both. In another embodiment, decomposition is induced by steam.

In another particular embodiment, the catalyst is partially decomposed using a decomposition method disclosed in PCT publication WO2004/046076, the entire disclosure of which is hereby incorporated herein by reference.

Hydrocarbon Oxidation

In one embodiment, the present invention includes a hydrocarbon oxidation process wherein one or more hydrocarbons are brought into contact with a source of oxygen in the presence of a radical initiator and the partially decomposed catalyst described herein. The process of the invention is suitable for oxidizing any hydrocarbon that is susceptible to oxidation.

In a particular embodiment, the radical initiator used in the process of the invention is an N-hydroxyimide compound. In a particular aspect of this embodiment, the N-hydroxyimide compound is selected from the group consisting of N-hydroxyphthalimide (NHPI), N-hydroxynaphthalimide (NHNI), N-hydroxysaccharin (NHSI), N-hydroxy quinolinic imide (NHQI), and derivatives thereof. In another particular aspect of this embodiment, the N-hydroxyimide compound is NHPI or an NHPI derivative selected from N-hydroxytetraphenylphthalimide ($Ph_4$NHPI); N-hydroxytetrachlorophthalimide ($Cl_4$NHPI); N-hydroxy,4-carboxyphthalimide (4-carboxyNHPI); and N-hydroxy, 4-sulfophthalimide (4-sulfoNHPI).

As shown in the examples below, the process is particularly suitable for the oxidation of dimethoxy methane (DMM) into dimethyl carbonate (DMC). Thus, in a particular embodiment, the invention provides a process for producing DMC, the process comprising oxidizing DMM in the presence of a radical initiator and a partially decomposed catalyst as described herein. In a particular aspect of this embodiment, the process of the invention results in at least 30%, or at least 31%, or at least 32%, or at least 35%, or at least 37%, or at least 40%, or at least 45%, or at least 48%, or at least 50% conversion of DMM. In another particular aspect of this embodiment, the selectivity rate for DMC is at least 60%, or at least 62%, or at least 65%, or at least 68%, or at least 70%, or at least 72%, or at least 74%, or at least 75%, or at least 77%.

In a particular embodiment, prior to oxidation, the DMM is produced using the well established process of acetalization of formaldehyde with methanol over zeolite.

The present invention is further illustrated by means of the following examples.

EXAMPLES $Cu(NO_3)_2 \cdot 3H_2O$, L-arginine, $Co(NO_3)_2 \cdot 6H_2O$, $Mn(NO_3)_2 \cdot 2H_2O$, $AuCl_3$, $AgNO_3$, $Zn(NO_3)_2 \cdot 6H_2O$, $Ni(NO_3)_2 \cdot 6H_2O$, and $Cr(NO_3)_3 \cdot 9H_2O$ used in the examples below are available from Sigma-Aldrich.

Chlorobenzene, acetonitrile, and acetone used in the examples below were pro analysis quality obtained from J. T. Baker.

DMM and DMC used in the examples below were obtained from Sigma-Aldrich.

NHPI used in the examples below was obtained from Fluka.

NHQI, $Ph_4$NHPI, and 4-sulfoNHPI used in the examples below were prepared by reacting the corresponding cyclic anhydride with hydroxylamine according to well known general literature procedures.

Example 1

Preparation of 5% Cu/SiO$_2$ Catalyst

Example 1a: 10.0 grams of a silica powdered support (surface area=270 m$^2$/g) was impregnated by incipient wetness with solution prepared by mixing 2.0 grams of $Cu(NO_3)_2 \cdot 3H_2O$, 11.6 grams of L-arginine, and enough water to form a total 10 cc solution volume. The sample was dried overnight at 100° C.

The Cu-arginine complex was then calcined in air to 250° C. at a rate of 4° C./min to form an organo-oxide Cu remnant. The decomposition pattern of the Cu-arginine complex, as measured by a TG/DTA trace, is shown in FIG. 1.

Figure 2:
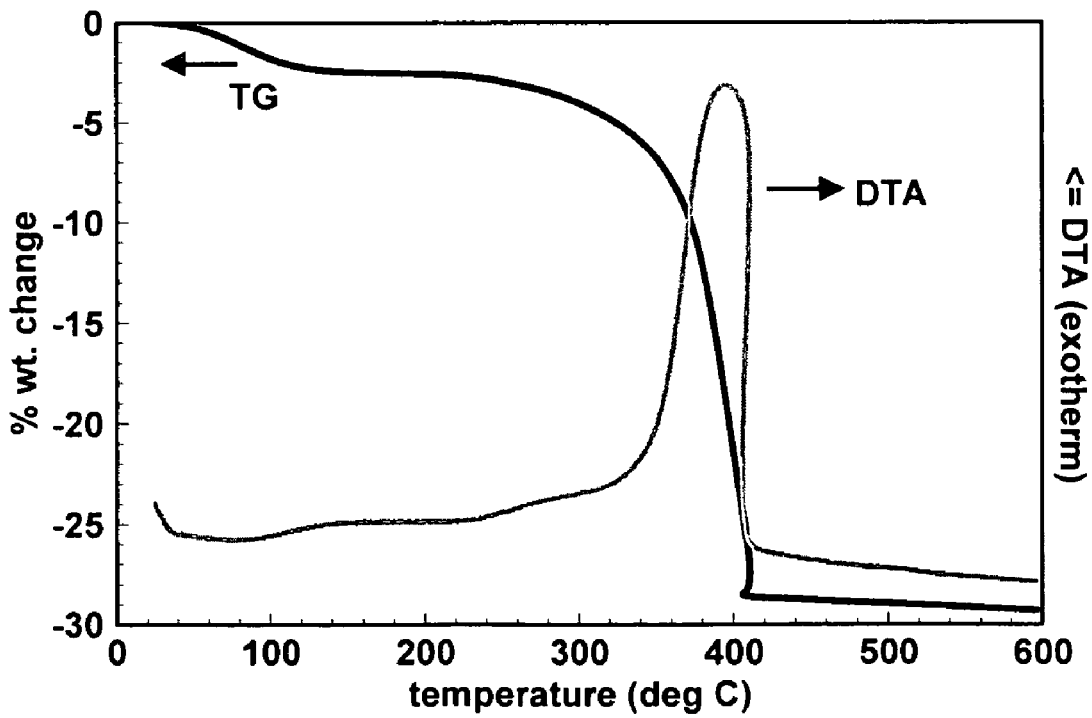
FIG. 2 shows the decomposition pattern of the Cu-arginine remnant prepared according to Example 1b, as measured by TG/DTA.

Example 1b: The organo-oxide Cu remnant was further decomposed by calcining the remnant in air to 600° C. The decomposition pattern of the organo-oxide Cu remnant, as measured by a TG/DTA trace, is shown in FIG. 2.

Example 2

Preparation of 5% CuO, 2% NiO/SiO$_2$ Catalyst (Partial Decomposition)

23.2 grams of a silica powdered support (surface area=270 m$^2$/g) was impregnated by incipient wetness with a solution prepared by mixing 3.8 grams of $Cu(NO_3)_2 \cdot 3H_2O$, 1.95 grams of $Ni(NO_3)_2 \cdot 6H_2O$, 15.87 grams of L-arginine, and enough water to form a total 19 cc solution volume. The sample was dried overnight at 100° C.

Figure 4:
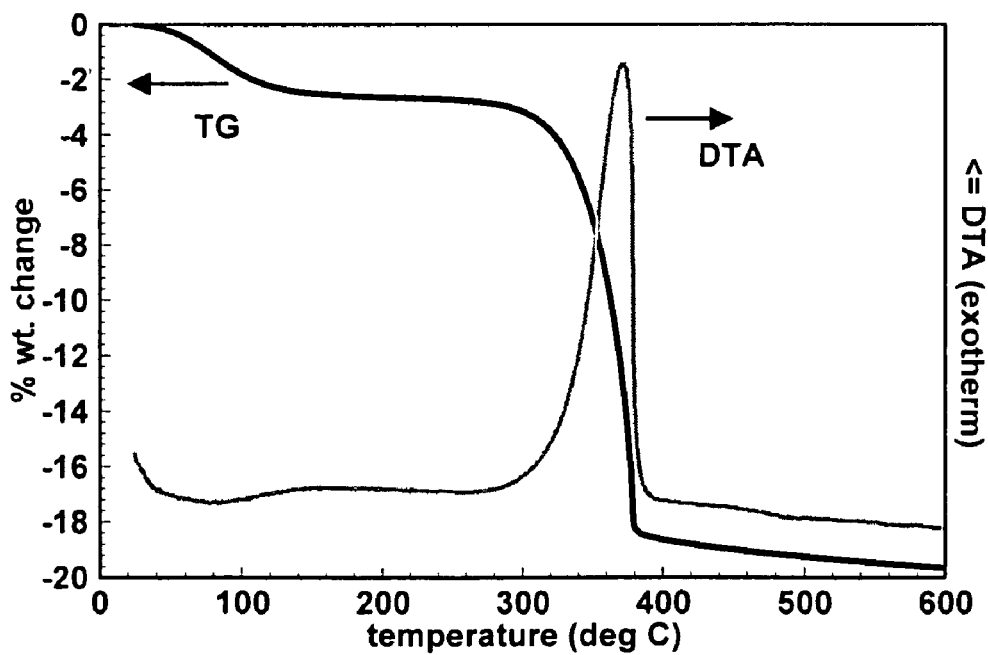
FIG. 4 shows the decomposition pattern of the 5% CuO, 2% $NiO/SiO_2$ remnant prepared according to Example 2, as measured by TG/DTA.

The resulting complex was then calcined in air to 275° C. at a rate of 4° C./min to form a remnant. The decomposition pattern of the complex, as measured by a TG/DTA trace, is shown in FIG. 4.

Example 3

Preparation of 5% CuO, 2% NiO/SiO$_2$ Catalyst (Full Decomposition)

A portion of the catalyst from Example 7 was calcined to 400° C. at a rate of 0.5° C./min, and then held at that temperature for 4 hours to remove all remnant organic phases.

Example 4

Preparation of 5% CuO, 2% NiO/SiO$_2$ Catalyst (No Organic Compound Used)

23.2 grams of a silica powdered support (surface area=270 m$^2$/g) was impregnated by incipient wetness with a solution prepared by mixing 3.8 grams of Cu(NO$_3$)$_2$.3H$_2$O, 1.95 grams of Ni(NO$_3$)$_2$.6H$_2$O, and enough water to form a total 19 cc solution volume. The sample was dried overnight at 100° C.

The resulting complex was then calcined in air to 350° C. at a rate of 4° C./min to form Cu—Ni oxide.

Example 5

Preparation of 31 mol % Solid CuO

A catalyst consisting of approximately 31 mol % Cu was prepared according to Japanese Patent 2000119225, the entire disclosure of which is hereby incorporated herein by reference.

Example 6

Preparation of 2 mole % Solid CuO

A catalyst consisting of approximately 2 mol % Cu was prepared according to Japanese Patent 2000119225, the entire disclosure of which is hereby incorporated herein by reference.

Example 7

Preparation of 5% CuO, 2% CoO/SiO$_2$ Catalyst 18.6 grams of a silica powdered support (surface area=270 m$^2$/g) was impregnated by incipient wetness with a solution prepared by mixing 3.03 grams of Cu(NO$_3$)$_2$.3H$_2$O, 1.55 grams of Co(NO$_3$)$_2$.6H$_2$O, 12.5 grams of L-arginine, and enough water to form a total 19 cc solution volume. The sample was dried overnight at 100° C.

Figure 3:
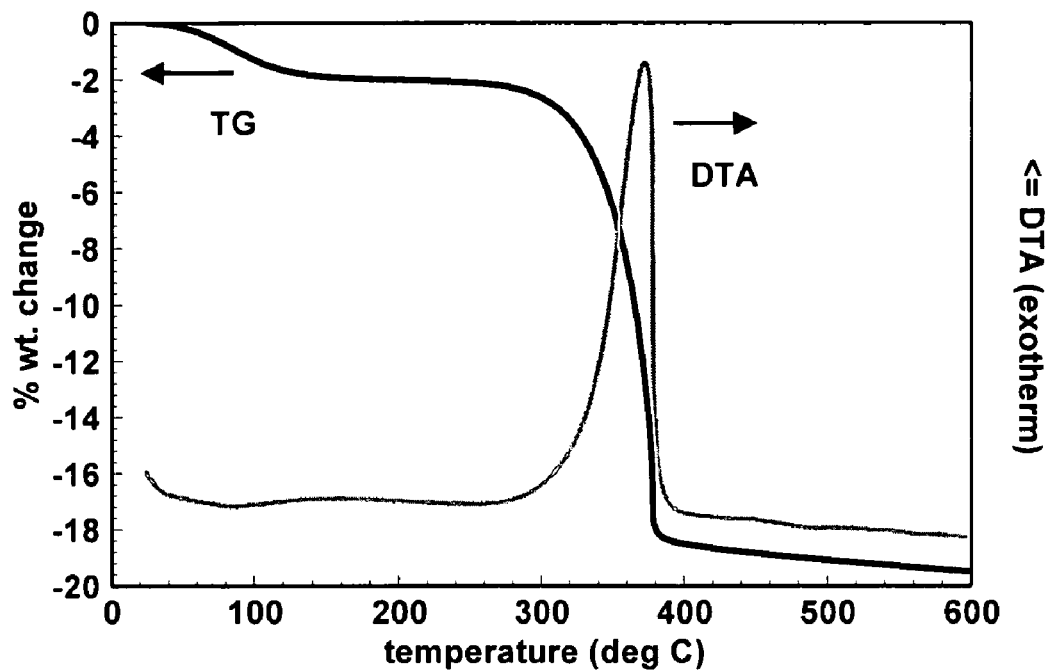
FIG. 3 shows the decomposition pattern of the Cu—Co remnant prepared according to Example 7, as measured by TG/DTA.

The resulting complex was then calcined in air to 275° C. at a rate of 4° C./min to form a remnant. The decomposition pattern of the complex, as measured by a TG/DTA trace, is shown in FIG. 3.

Example 8

Preparation of 5% CuO, 2% MnO/SiO$_2$ Catalyst 23.2 grams of a silica powdered support (surface area=270 m$^2$/g) was impregnated by incipient wetness with a solution prepared by mixing 3.8 grams of Cu(NO$_3$)$_2$.3H$_2$O, 1.3 grams of Mn(NO$_3$)$_2$.2H$_2$O, 15.87 grams of L-arginine, and enough water to form a total 23 cc solution volume. The sample was dried overnight at 100° C.

The resulting complex was then calcined in air to 275° C. at a rate of 4° C./min to form a remnant.

Example 9

Preparation of 5% CuO, 1% AuO$_5$/SiO$_2$ Catalyst 18.8 grams of a silica powdered support (surface area=270 m$^2$/g) was impregnated by incipient wetness with a solution prepared by mixing 3.03 grams of Cu(NO$_3$)$_2$.3H$_2$O, 0.3 grams of AuCl$_3$, 9.4 grams of L-arginine, and enough water to form a total 19 cc solution volume. The sample was dried overnight at 100° C.

The resulting complex was then calcined in air to 275° C. at a rate of 4° C./min to form a remnant.

Example 10

Preparation of 5% CuO, 1% AgO$_5$/SiO$_2$ Catalyst 18.8 grams of a silica powdered support (surface area=270 m$^2$/g) was impregnated by incipient wetness with a solution prepared by mixing 3.03 grams of Cu(NO$_3$)$_2$.3H$_2$O, 0.3 grams of AgNO$_3$, 9.96 grams of L-arginine, and enough water to form a total 19 cc solution volume. The sample was dried overnight at 100° C.

The resulting complex was then calcined in air to 275° C. at a rate of 4° C./min to form a remnant.

Example 11

Preparation of 5% CuO, 2% ZnO/SiO$_2$ Catalyst 23.2 grams of a silica powdered support (surface area=270 m$^2$/g) was impregnated by incipient wetness with a solution prepared by mixing 3.8 grams of Cu(NO$_3$)$_2$.3H$_2$O, 1.8 grams of Zn(NO$_3$)$_2$.6H$_2$O, 15.87 grams of L-arginine, and enough water to form a total 23 cc solution volume. The sample was dried overnight at 100° C.

The resulting complex was then calcined in air to 275° C. at a rate of 4° C./min to form a remnant.

Example 12

Preparation of 5% CuO, 1% CrO/SiO$_2$ Catalyst 20.0 grams of a silica powdered support (surface area=270 m$^2$/g) was impregnated by incipient wetness with a solution prepared by mixing 4.04 grams of Cu(NO$_3$)$_2$.3H$_2$O, 1.63 grams of Cr(NO$_3$)$_3$.9H$_2$O, and 14.6 grams of L-arginine, and enough water to form a total 20 cc solution volume. The sample was dried overnight at 100° C.

The resulting complex was then calcined in air to 250° C. at a rate of 4° C./min to form a remnant.

Oxidation Examples 13-19

Production of DMC Using Various Copper Catalysts

The catalyst prepared in Example 2 above was used to produce DMC in Examples 14 and 15. The catalysts prepared in Examples 3, 4, 5, and 6 above were used to produce DMC in Examples 16, 17, 18, and 19, respectively. Silica support material was used alone as the catalytic material in Example 13. The experiments were carried out as follows: 0.1 mol DMM (except in Example 15, where 50 mmol DMM was used), 10 mmol chlorobenzene, 70 ml acetonitrile, 5 mmol N-hydroxyphthalimide (NHPI), and 2.5 grams of catalyst were charged to a 170 ml Hastalloy C autoclave. The pressure was raised to 80 bar 8% O$_2$/N$_2$. The conversion and selectivity rates were analyzed by gas chromatography according to the following procedure. Samples were diluted with diethyl ether (and reduced with Ph$_3$P where peroxide was present), and measured on a wax-column using predetermined response factors: dimethoxymethane 0.258, methyl formate (MeF) 0.149, methanol (MeOH) 0.137, dimethyl carbonate (DMC) 0.190, methoxymethyl formate (MMF) 0.170, all relative to chlorobenzene. The results of the gas chromatography analysis are given in Table 1.

Table 1 shows the conversion and selectivity rates of the following catalyst materials: silica support material alone (Example 13), a Cu/Ni catalyst including a partially decomposed organic complex according to the invention (Examples 14 and 15), a fully decomposed Cu/Ni catalyst (Example 16), a Cu/Ni catalyst without an organic complex (Example 17), and 31 mol % and 2 mol % solid CuO catalysts (Examples 18 and 19).

TABLE 1

| Oxidation Example No. | Catalyst prepared according to (Example No.) | Conversion (%) 1st hour | Conversion (%) 2nd hour | Selectivity (%) DMC | Selectivity (%) MeF/MeOH | Selectivity (%) MMF |
|---|---|---|---|---|---|---|
| 13 | pure $SiO_2$ | 3 | 19 | 28 | 51 | 11 |
| 14 | partially decomposed 5% CuO, 2% $NiO/SiO_2$ (2) | 22 | 31 | 65 | 25 | 10 |
| 15** | partially decomposed 5% CuO, 2% $NiO/SiO_2$ (2) | * | 43 | 65 | 27 | 8 |
| 16 | fully decomposed 5% CuO, 2% $NiO/SiO_2$ (3) | 18 | 27 | 41 | 47 | 13 |
| 17 | 5% CuO, 2% $NiO/SiO_2$ no organic (4) | 20 | 34 | 24 | 63 | 13 |
| 18 | 31 mole % solid CuO (5) | 3 | 26 | 59 | 26 | 14 |
| 19 | 2 mole % solid CuO (6) | <1 | 9 | 48 | 27 | 18 |

*not measured

**50 mmol DMM used, compared to 0.1 mol DMM used in Examples 13, 14, and 16-19

Oxidation Examples 20-25

Production of DMC Using Various Metals as Cocatalysts

The catalysts prepared in Examples 7, 8, 9, 10, 11, and 12 were used to produce DMC in Examples 20, 21, 22, 23, 24, and 25, respectively. The experiments were carried out as follows: 0.1 mol DMM, 10 mmol chloro-benzene, 70 ml acetonitrile, 5 mmol N-hydroxyphthalimide (NHPI), and 2.5 grams of catalyst were charged to a 170 ml Hastalloy C autoclave. The pressure was raised to 80 bar 8% $O_2/N_2$ (except in example 21, where only 72 bar $O_2/N_2$ was available), followed by calcining to 80° C. for one hour and to 100° C. for an additional hour. The conversion and selectivity rates were analyzed by gas chromatography according to the following procedure. Samples were diluted with diethyl ether (and reduced with $Ph_3P$ where peroxide was present), and measured on a wax-column using predetermined response factors: dimethoxymethane 0.258, methyl formate (MeF) 0.149, methanol (MeOH) 0.137, dimethyl carbonate (DMC) 0.190, methoxymethyl formate (MMF) 0.170, all relative to chlorobenzene. The results of the gas chromatography analysis are given in Table 2; the results from Example 14 above are also given in Table 2 for comparison purposes.

Oxidation Examples 26-31

Production of DMC Using Various NHPI-Type Compounds as Radical Initiators

The catalyst prepared in Example 2 above was used to produce DMC in Examples 26-31, using various NHPI-type compounds as radical initiators. The experiments were carried out as follows: 20 mmol DMM, 1 mmol chloro-benzene, 20 ml acetonitrile (except in examples 30 & 31 where acetone was used as the solvent), and the radical initiator compound and catalyst in the amounts given in Table 3, were charged to a 170 ml Hastalloy C autoclave. The pressure was raised to 40 bar 8% $O_2/N_2$, followed by calcining according to the conditions given in Table 3. The conversion and selectivity rates were analyzed by gas chromatography according to the following procedure. Samples were diluted with diethyl ether (and reduced with $Ph_3P$ where peroxide was present), and measured on a wax-column using predetermined response factors: dimethoxymethane 0.258, methyl formate (MeF) 0.149, methanol (MeOH) 0.137, dimethyl carbonate (DMC) 0.190, methoxymethyl formate (MMF) 0.170, all relative to chlorobenzene. The results of the gas chromatography analysis are given in Table 3.

TABLE 2

| Oxidation Example No. | Catalyst prepared according to (Example No.) | Conversion (%) 1st hour | Conversion (%) 2nd hour | Selectivity (%) DMC | Selectivity (%) MeF/MeOH | Selectivity (%) MMF |
|---|---|---|---|---|---|---|
| 14 | 5% CuO, 2% $NiO/SiO_2$ (2) | 22 | 31 | 65 | 25 | 10 |
| 20 | 5% CuO, 2% $CoO/SiO_2$ (7) | 29 | 31 | 44 | 44 | 12 |
| 21 | 5% CuO, 2% $MnO/SiO_2$ (8) | 8 | 32 | 59 | 28 | 12 |
| 22 | 5% CuO, 1% $AuO_{.5}/SiO_2$ (9) | 16 | 31 | 59 | 27 | 13 |
| 23 | 5% CuO, 1% $AgO_{.5}/SiO_2$ (10) | 12 | 33 | 58 | 29 | 13 |
| 24 | 5% CuO, 2% $ZnO/SiO_2$ (11) | 10 | 31 | 62 | 27 | 12 |
| 25 | 5% CuO, 1% $CrO/SiO_2$ (12) | 16 | 33 | 58 | 32 | 10 |

TABLE 3

| Oxidation Example No. | Promoter | Catalyst | Conditions Time/Temperature | Conversion (%) | Selectivity (%) | | |
|---|---|---|---|---|---|---|---|
| | | | | | DMC | MeF/MeOH | MMF |
| 26 | 5% NHQI | 2% CuNi-org/SiO$_2$ | 2 hr/100° C. | 20 | 33 | 50 | 16 |
| 27 | 5% 4-sulfoNHPI | 4% CuNi-org/SiO$_2$ | 2 hr/70° C. | <11 | 0 | 0 | 0 |
| 28 | 5% NHPI | 2% CuNi-org/SiO$_2$ | 3 hr/100° C. | 50 | 70 | 21 | 9 |
| 29 | 5% Ph$_4$NHPI | 2% CuNi-org/SiO$_2$ | 3 hr/100° C. | 46 | 77 | 15 | 8 |
| 30 | 5% Ph$_4$NHPI | 2% CuNi-org/SiO$_2$ | 18 hr/100° C. | 11 | 71 | 23 | 6 |
| 31 | 1% Ph$_4$NHPI | 2% CuNi-org/SiO$_2$ | 5.5 hr/100° C. | <2 | 75 | * | * |

* not measured

All patents, test procedures, and other documents cited herein, including priority documents, are fully incorporated by reference to the extent such disclosure is not inconsistent with this invention and for all jurisdictions in which such incorporation is permitted.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the invention, including all features which would be treated as equivalents thereof by those skilled in the art to which the invention pertains.

When numerical lower limits and numerical upper limits are listed herein, ranges from any lower limit to any upper limit are contemplated.

What is claimed is:

1. A hydrocarbon oxidation process comprising bringing one or more hydrocarbons into contact with a source of oxygen in the presence of a radical initiator and a partially decomposed catalyst, to partially decomposed catalyst comprising:
   (a) a support; and
   (b) an organic metal complex comprising:
      (i) an organic compound comprising an amine, an amino acid, an amino alcohol or combinations thereof, and
      (ii) a metal-based compound, wherein the metal is selected from the group consisting of copper, nickel, and combinations thereof;
   wherein at least 5% of the organic compound remains in the catalyst.

2. The process of claim 1, wherein the one or more hydrocarbons comprises an ether.

3. The process of claim 2, wherein the ether is dimethoxymethane.

4. The process of claim 1, wherein the radical initiator is selected from the group consisting of N-hydroxyphthalimide (NHPI), N-hydroxynaphthalimide (NHNI), N-hydroxysaccharin (NHSI), N-hydroxy quinolinic imide (NHQI), and derivatives thereof.

5. The process of claim 3, wherein the radical initiator is selected from the group consisting of N-hydroxyphthalimide (NHPI), N-hydroxynaphthalimide (NHNI), N-hydroxysaccharin (NHSI), N-hydroxy quinolinic imide (NHQI), and derivatives thereof.

6. The process of claim 1, wherein the radical initiator is an NHPI-type compound selected from the group consisting of NHPI, N-hydroxytetraphenylphthalimide (Ph$_4$NHPI); N-hydroxytetrachlorophthalimide (Cl$_4$NHPI); N-hydroxy,4-carboxylphthalimide (4-carboxyNHPI); and N-hydroxy,4-sulfophthalimide (4-sulfoNHPI).

7. The process of claim 3, wherein the radical initiator is an NHPI-type compound selected from the group consisting of NHPI, N-hydroxytetraphenylphthalimide (Ph$_4$NHPI); N-hydroxytetrachlorophthalimide (Cl$_4$NHPI); N-hydroxy,4-carboxylphthalimide (4-carboxyNHPI); and N-hydroxy, 4-sulfophthalimide (4-sulfoNHPI).

8. The process of claim 1, wherein the radical initiator is N-hydroxytetraphenylphthalimide (Ph$_4$NHPI).

9. The process of claim 1, wherein the organic metal complex comprises an amino acid.

10. The process of claim 1, wherein the organic metal complex comprises a Cu-based compound.

11. The process of claim 1, wherein the organic metal complex comprises an amino acid and a Cu-based compound.

12. The process of claim 1, wherein the organic metal complex comprises a Cu/Ni-based compound.

13. The process of claim 12, wherein the organic metal complex comprises an amino acid.

14. The process of claim 13, wherein the amino acid is L-arginine.

15. The process of claim 1, wherein the catalyst support comprises silica.

16. A process for producing dimethyl carbonate (DMC), the process comprising contacting dimethoxy methane (DMM) with a source of oxygen in the presence of a radical initiator and a partially decomposed catalyst, the partially decomposed catalyst comprising:
   (a) a support; and
   (b) an organic metal complex comprising:
      (i) an organic compound comprising an amine, an amino acid, an amino alcohol or combinations thereof, and
      (ii) a metal-based compound, wherein the metal is selected from the group consisting of cooper, nickel, and combinations thereof:
   wherein at least 5% of the organic compound remains in the catalyst.

17. The process of claim 16, wherein the radical initiator is an NHPI-type compound selected from the group consisting NHPI, N-hydroxytetraphenylphthalimide (Ph$_4$NHPI); N-hydroxytetrachlorophthalimide (Cl$_4$NHPI); N-hydroxy,4-carboxylphthalimide (4-carboxyNHPI); and N-hydroxy,4-sulfophthalimide (4-sulfoNHPI).

18. The process of claim 16, wherein the radical initiator is N-hydroxytetraphenylphthalimide (Ph$_4$NHPI).

19. The process of claim 16, wherein the organic metal complex comprises an ammo acid.

20. The process of claim 19, wherein the organic metal complex comprises a Cu/Ni-based compound.

21. The process of claim 16, wherein the oxidation reaction is conducted at a temperature of from 20° C. to 250° C. and a pressure of from 1 to 100 atm.

22. A partially decomposed catalyst comprising:
(a) a silica support; and
(b) an organic metal complex comprising:
  (i) an organic compound comprising an amine, an amino acid, an amino alcohol or combinations thereof, and
  (ii) a metal-based compound, wherein the metal is selected from the group consisting of copper, nickel, and combinations thereof;
wherein at least 5% of the organic compound remains in the catalyst.

23. The catalyst of claim 22, wherein the amino acid is chosen from natural and synthetic amino acids.

24. The catalyst of claim 23, wherein the natural amino acid is L-arginine.

25. The catalyst of claim 22, wherein the amino alcohol is chosen from mono-, di-, and tri-, substituted aliphatic hydroxyalkylamines, N-alkyl-methanolamines, N-alkyl-dimethanolamines, N,N-dialkyl-ethanolamines, N-alkyl-propanolamines, N-alkyl-dipropanolamines, N,N-dialkyl-propanolamines, N-alkyl-butanolamines, N-alkyl-dibutanolamines, N,N-dialkyl-butanolamines, N-alkyl-hexanolamines, N-alkyl-dihexanolamines, N,N-dialkyl-hexanolamines, N-alkyl-heptanolamines, N-alkyl-diheptanolamines, and N,N-dialkyl-heptanolamines.

26. The catalyst of claim 22, wherein the metal is copper and the metal-based compound is a copper salt.

27. The catalyst of claim 26, wherein the copper salt is copper nitrate.

28. The catalyst of claim 22, wherein the organic metal complex comprises an additional metal-based compound.

29. The catalyst of claim 26, wherein the organic metal complex comprises an additional metal-based compound.

30. The catalyst of claim 29, wherein the additional metal-based compound is a nickel salt.

31. The catalyst of claim 30, wherein the metal-based compound is copper nitrate and the additional metal-based compound is nickel nitrate.

32. The catalyst of claim 22, wherein the catalyst is an oxidation catalyst.

33. A process for the manufacture of a partially decomposed catalyst, the process comprising:
(a) preparing a catalyst precursor comprising:
  a support; and
  an organic metal complex comprising:
    (i) an organic compound comprising an amine, an amino acid, an amino alcohol or combinations thereof, and
    (ii) a metal-based compound, wherein the metal is selected from the group consisting of copper, nickel, and combinations thereof; and
(b) partially decomposing organic compound to form the partially decomposed catalyst, wherein at least 5% of the organic compound remains in the catalyst.

34. The process of claim 33, wherein the catalyst precursor is prepared by contacting simultaneously the support, the organic compound, a Cu-based compound, and optionally another metal-based compound.

35. The process of claim 33, wherein the catalyst precursor is prepared by contacting simultaneously the support, the organic compounds, a Cu-based compound, and a Ni-based compound.

36. The process of claim 33, wherein the catalyst precursor is prepared by:
(a) mixing the organic compound, a Cu-based compound, water, and optionally another metal-based compound to form a solution; and
(b) impregnating the solution onto the support.

37. The process of claim 33, wherein the catalyst precursor is prepared by:
(a) mixing the organic compounds, a Cu-based compound, a Ni-based compound, and water to form a solution; and
(b) impregnating the solution onto a solid support.

38. The process of claim 33, wherein the organic compounds is partially decomposed with heat.

39. A process for the manufacture of a partially decomposed catalyst, the process comprising:
(a) mixing L-arginine, a Cu-based compound, water, and optionally another metal-based compound to form a solution;
(b) impregnating the solution onto a silica support to form a catalyst precursor;
(c) partially decomposing the L-arginine to form the catalyst, wherein at least 5% of L-arginine remains in the catalyst.

40. The process of claim 39, wherein the solution is formed by mixing L-arginine, a Cu-based compound, water, and a Ni-based compound.

41. The process of claim 39, wherein the catalyst is made in a fixed bed, batch, catalytic distillation reactor.

42. The catalyst of claim 22, wherein the amine is chosen from aliphatic amines, cycloaliphatic amines, aralkyl amines, and alkaryl amines.

43. The catalyst of claim 22, wherein the catalyst is used for hydrocarbon oxidation.

44. The catalyst of claim 43, wherein the catalyst is used for oxidation of dimethoxy methane (DMM) into dimethyl carbonate (DMC).

45. The catalyst of claim 22, wherein the support is chosen from alumina, silica, activated carbon, silicon carbide, aluminum oxide, silicon dioxide, titanium dioxide, zirconium dioxide, magnesium oxide, zinc oxide, and combinations thereof.

* * * * *